(12) United States Patent
Nasarabadi et al.

(10) Patent No.: US 7,972,818 B2
(45) Date of Patent: *Jul. 5, 2011

(54) FLOW CYTOMETRIC DETECTION METHOD FOR DNA SAMPLES

(75) Inventors: Shanavaz Nasarabadi, Livermore, CA (US); Richard G. Langlois, Livermore, CA (US); Kodumudi S. Venkateswaran, Round Rock, TX (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/454,478

(22) Filed: Jun. 16, 2006

(65) Prior Publication Data

US 2007/0117110 A1    May 24, 2007

Related U.S. Application Data

(63) Continuation-in-part of application No. 10/077,321, filed on Feb. 14, 2002, now Pat. No. 7,083,951.

(60) Provisional application No. 60/268,852, filed on Feb. 14, 2001.

(51) Int. Cl.
| | |
|---|---|
| *C12P 19/34* | (2006.01) |
| *C12Q 1/68* | (2006.01) |
| *C12N 9/00* | (2006.01) |
| *C12M 1/34* | (2006.01) |
| *C07H 21/04* | (2006.01) |

(52) U.S. Cl. ........ 435/91.2; 435/6; 435/183; 435/287.2; 536/23.1; 536/24.3; 536/24.33

(58) Field of Classification Search .................. None
See application file for complete search history.

(56) References Cited

U.S. PATENT DOCUMENTS

| | | | | |
|---|---|---|---|---|
| 6,184,379 B1 * | 2/2001 | Josel et al. | ...................... | 546/48 |
| 7,083,951 B2 * | 8/2006 | Nasarabadi et al. | .......... | 435/91.2 |
| 7,148,280 B2 * | 12/2006 | Leon et al. | .................... | 524/428 |
| 2005/0260676 A1 * | 11/2005 | Chandler et al. | .................. | 435/6 |

OTHER PUBLICATIONS

Luminex 100 IS User Manual Version 2.3, 2001, pp. 1-230.*
Website Wikipedia.com; definition of Forster resonance eneergy transfer, pp. 1-7, visited May 19, 2010.*
W.J. Wilson et al "A Multiplexed PCR-coupled liquid bead array for the simultaneous detection of four biothreat agents" , Molecular and Cellular Probes, Apr. 2005;19(2): 137-144.
B.J. Hindson et al "Autonomous Detection of Aerosolized Biological Agents by Multiplexed Immunoassay with Polymerase Chain Reaction Confirmation", Anal Chem, Jan. 2005; 77(1): 284-289.
J.A. Higgins et al "A Handheld Real Time Thermal Cycler for Bacterial Pathogen Detection", Biosens Bioelectron, Aug. 2003; 18(9): 1115-11123.
C.J.Elkin et al "A Reusable Flow-Trough Polymerase Chain Reaction Instrument for the Continuous Monitoring of Infectious Biological Agents" Anal. Chem vol. 75; No. 14 Jul. 15, 2003; 3446-3450.
Spiro et al., "A Bead-Based Method for Multiplexed Identification and Quantitation of DNA Sequences Using Flow Cytometry", vol. 66, No. 10, pp. 4258-4265, Oct. 2000.
Iannone et al., "Multiplexed Single Nucleotide Polymorphism Genotyping by Oligonucleotide Ligation and Flow Cytometry", pp. 131-140, Oct. 31, 1999.
Armstrong et al., "Suspension Arrays for High Throughput, Multiplexed Single Nucleotide Polymorphism Genotyping", pp. 102-108, Jan. 20, 2000.
Holland et al., "Detection of specific polymerase chain reaction product by utilizing the 5'→3' exonuclease activity of *Thermus aquaticus*", vol. 88, pp. 7276-7280, Aug. 1991.

* cited by examiner

*Primary Examiner* — Bradley L Sisson
(74) *Attorney, Agent, or Firm* — Eddie E. Scott; James S. Tak

(57) ABSTRACT

Disclosed herein are two methods for rapid multiplex analysis to determine the presence and identity of target DNA sequences within a DNA sample. Both methods use reporting DNA sequences, e.g., modified conventional Taqman® probes, to combine multiplex PCR amplification with microsphere-based hybridization using flow cytometry means of detection. Real-time PCR detection can also be incorporated. The first method uses a cyanine dye, such as, Cy3™, as the reporter linked to the 5' end of a reporting DNA sequence. The second method positions a reporter dye, e.g., FAM™ on the 3' end of the reporting DNA sequence and a quencher dye, e.g., TAMRA™, on the 5' end.

10 Claims, 4 Drawing Sheets

FAM

TAMRA

FLOW CYTOMETRIC DETECTION METHOD FOR DNA SAMPLES

I. CROSS-REFERENCE TO RELATED APPLICATIONS

Figure 1:
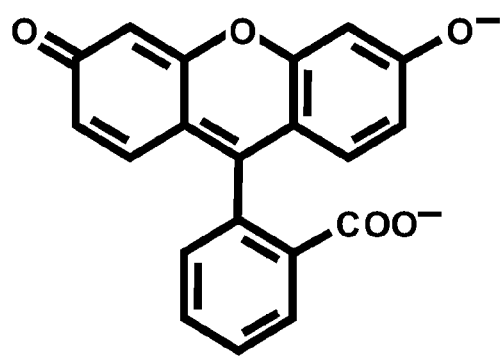

This application is a Continuation-in-Part of U.S. patent application Ser. No. 10/077,321 now U.S. Pat. No. 7,083,951 filed Feb. 14, 2002 entitled "A Flow Cytometric Detection Method for DNA Samples" which claims priority to Provisional Patent Application 60/268,852 filed Feb. 14, 2001 entitled, "Rapid Multiplex Flow Cytometric Detection of Nucleic Acid Amplified Products" both of which are incorporated herein in their entirety by this reference.

The United States Government has rights in this invention pursuant to Contract No. W-7405-ENG-48 between the United States Department of Energy and the University of California for the operation of Lawrence Livermore National Laboratory.

II. BACKGROUND OF THE INVENTION

Bead based hybridization assays have been reported for multiplexed detection of PCR amplified products. Each published method is well suited to a specific application. Published bead based hybridization assays require more than one step for hybridization, are time consuming and are not easily automated.

In a method disclosed by Brown et al, *A Bead-Based Method for Multiplexed Identification and Quantitation of DNA Sequences Using Flow Cytometry*, Applied and Environmental Microbiology, Oct: 4258-4265, (2000), a double stranded amplified DNA is enzymatically digested with Shrimp alkaline phosphatase (SAP) and Exonuclease 1. The single stranded DNA produced from the digestion is then annealed to an oligonucleotide on a bead and the hybridized product is detected with the Luminex™ flow analyzer.

Weiner et al, *Multiplexed Single Nucleotide Polymorphism Genotyping by Oligonucleotide Ligation and Flow Cytometry*, Cytometry 39:131-140 (2000), describes a universal Zip Code hybridization method. In this method, a complementary Zip Code sequence is attached to a long piece of DNA that is attached to a spacer used to reduce the stearic hindrance. A part of the allele complementary sequence is attached to the Zip Code sequence. A capture probe is then prepared by hybridization and ligation of the allele complementary sequence and a fluorescently labeled allele complementary sequence in the presence of the single stranded amplified DNA and ligase enzyme.

In *Suspension Arrays for High Throughput, Multiplexed single Nucleotide Polymorphism Genotyping*, Cytometry 40:102-108 (2000), Muzumder et al describes a more simplistic, but difficult approach. Their approach denatures a fluorescently labeled denatured PCR product and directly hybridizes that product to complementary oligonucleotides attached to beads.

Each of the above mentioned assays take on average several hours to go from amplification to detection. Holland et al in, *Detection of specific polymerase chain reaction product by utilizing the 5'-3' exonuclease activity of Thermus aquaticus DNA polymerase*, Proc Natl Acad Sci U S A 88 (16):7276-80, (1991), discloses real time PCR amplification. This method is generally referred to as Taqman® real time detection and is routinely used for real-time PCR amplification. Real time PCR amplification is measured using fluorogenic probes that can detect the 5'-exonuclease activity of the DNA polymerase. At present, Taqman® real time detection can simultaneously detect a maximum of four nucleic acid targets.

IV. SUMMARY OF THE INVENTION

Aspects of the invention include a method for multiplexed detection of PCR amplified products comprising: providing at least one DNA sample for a sample multiplex PCR amplification reaction, providing necessary reagents and primers for the sample multiplex PCR amplification reaction and a background multiplex PCR amplification reaction, forming a sample PCR product by conducting the sample multiplex PCR amplification reaction using at least one reporting DNA sequence complementary to a region on at least one target DNA sequence, wherein the reporting DNA sequence has a fluorophore on the 5' end, forming a background PCR product by conducting the background multiplex PCR amplification reaction, wherein the background PCR amplification reaction is run under the same conditions and using the same primers and reagents as the sample PCR amplification reaction, forming a microsphere mix comprising a plurality of optically encoded microspheres bound to a plurality of oligonucleotides, wherein each optical code corresponds to specific oligonucleotide having a DNA sequence complementary to at least one reporting DNA sequence, forming a sample hybridization product by adding the sample PCR product to the microsphere mix, forming a background hybridization product by adding the background PCR product to the microsphere mix, determining the existence of the target DNA sequence specified by the reporting DNA sequence by comparing the fluorescence of the sample hybridization product with the background hybridization product using flow cytometry.

Another aspect of the invention includes a method for multiplexed detection of PCR amplified products comprising: providing at least one DNA sample for a sample multiplex PCR amplification reaction, providing necessary reagents and primers for the sample multiplex PCR amplification reaction and a background multiplex PCR amplification reaction, forming a sample PCR product by conducting the sample multiplex PCR amplification reaction using at least one reporting DNA sequence complementary to a region on at least one target DNA sequence, wherein the reporting DNA sequence has a fluorophore on the 5' end and a quencher on the 3' end, forming a background PCR product by conducting the background multiplex PCR amplification reaction, wherein the background PCR amplification reaction is run under the same conditions and using the same primers, reagents and reporting DNA sequences as the sample PCR amplification reaction, determining with on-line fluorescence detecting means whether a difference in fluorescence exists between the sample PCR product and the background PCR product, the difference being indicative of the multiplex PCR amplification reaction resulting in the formation of (1) at least one PCR amplification product and (2) at least one residual reporting sequence containing the quencher, forming a microsphere mix comprising a plurality of optically encoded microspheres bound to a plurality of oligonucleotides, wherein each optical code corresponds to specific oligonucleotide having a DNA sequence complementary to at least one reporting DNA sequence, forming a sample hybridization product by adding the sample PCR product to the microsphere mix, forming a background hybridization product by adding the background PCR product to the microsphere mix, determining the existence of the target DNA sequence specified by the reporting DNA sequence by comparing the fluorescence of the sample hybridization product with the background hybridization product using flow cytometry.

Another aspect of the invention includes a method for multiplexed detection of PCR amplified products comprising: providing at least one DNA sample for a sample multiplex PCR amplification reaction, providing necessary reagents and primers for the sample multiplex PCR amplification reaction and a background multiplex PCR amplification reaction, forming a sample PCR product by conducting the sample multiplex PCR amplification reaction using at least one reporting DNA sequence complementary to a region on at least one target DNA sequence, wherein the reporting DNA sequence has a quencher on the 5' end and a fluorophore on the 3' end, forming a background PCR product by conducting the background multiplex PCR amplification reaction, wherein the background PCR amplification reaction is run under the same conditions and using the same primers, reagents and reporting DNA sequences as the sample PCR amplification reaction, determining with on-line fluorescence detecting means whether a difference in fluorescence exists between the sample PCR product and the background PCR product, the difference being indicative of the multiplex PCR amplification reaction resulting in the formation of (1) at least one PCR amplification product and (2) at least one residual reporting sequence containing the fluorophore, forming a microsphere mix comprising a plurality of optically encoded microspheres bound to a plurality of oligonucleotides, wherein each optical code corresponds to. specific oligonucleotide having a DNA sequence complementary to at least one reporting DNA sequence, forming a sample hybridization product by adding the sample PCR product to the microsphere mix, forming a background hybridization product by adding the background PCR product to the microsphere mix, determining the existence of the target DNA sequence specified by the reporting DNA sequence by comparing the fluorescence of the sample hybridization product with the background hybridization product using flow cytometry.

V. BRIEF DESCRIPTION OF THE DRAWINGS

Figure 2:
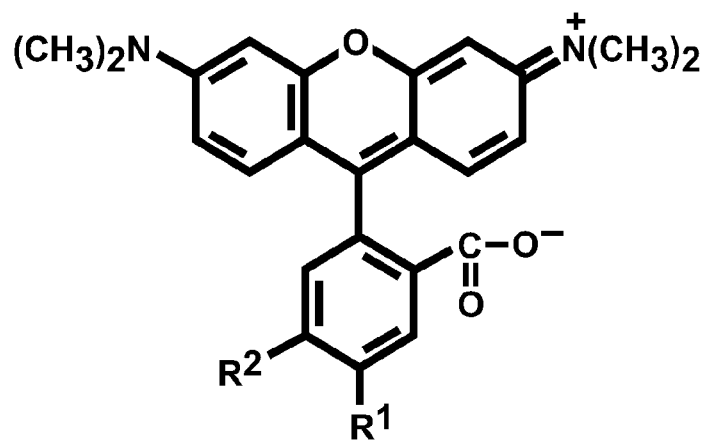
Figure 3:
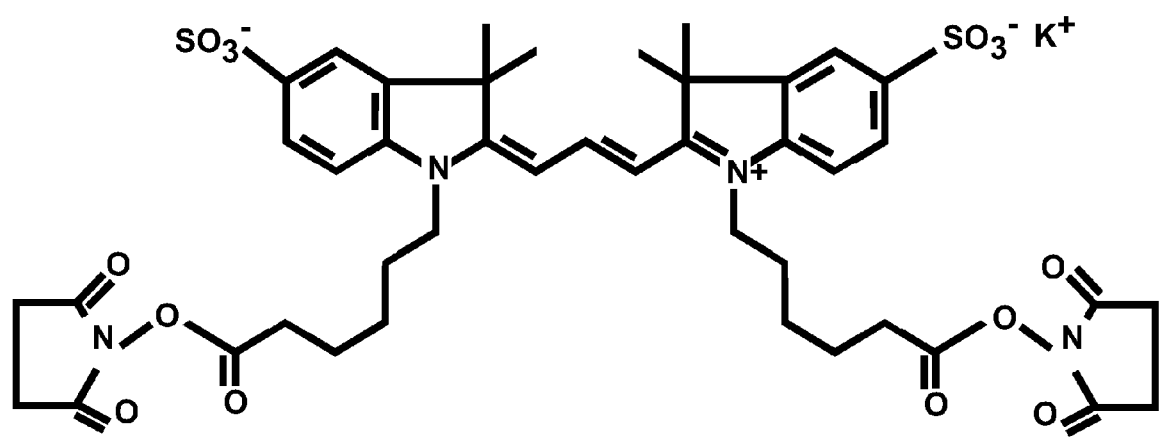
Figure 4:
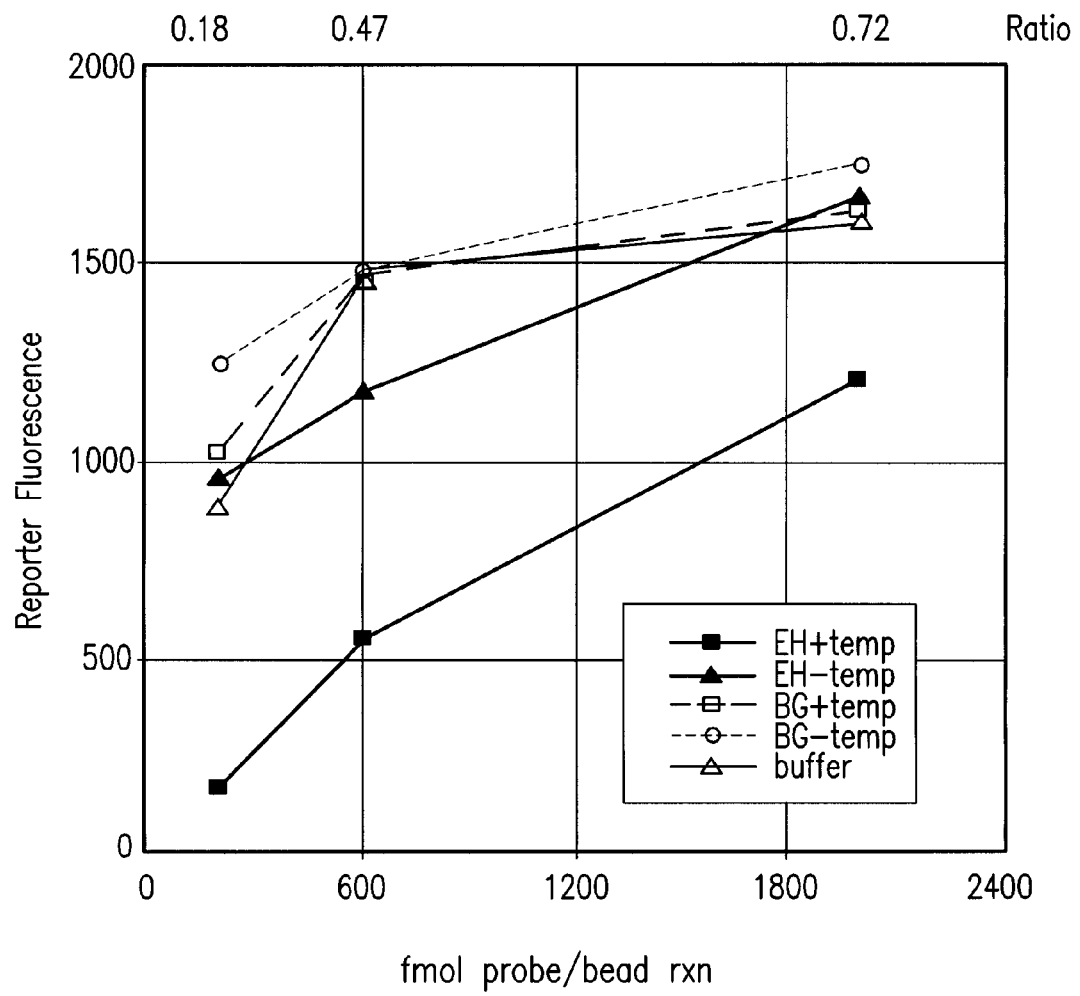
Figure 5:
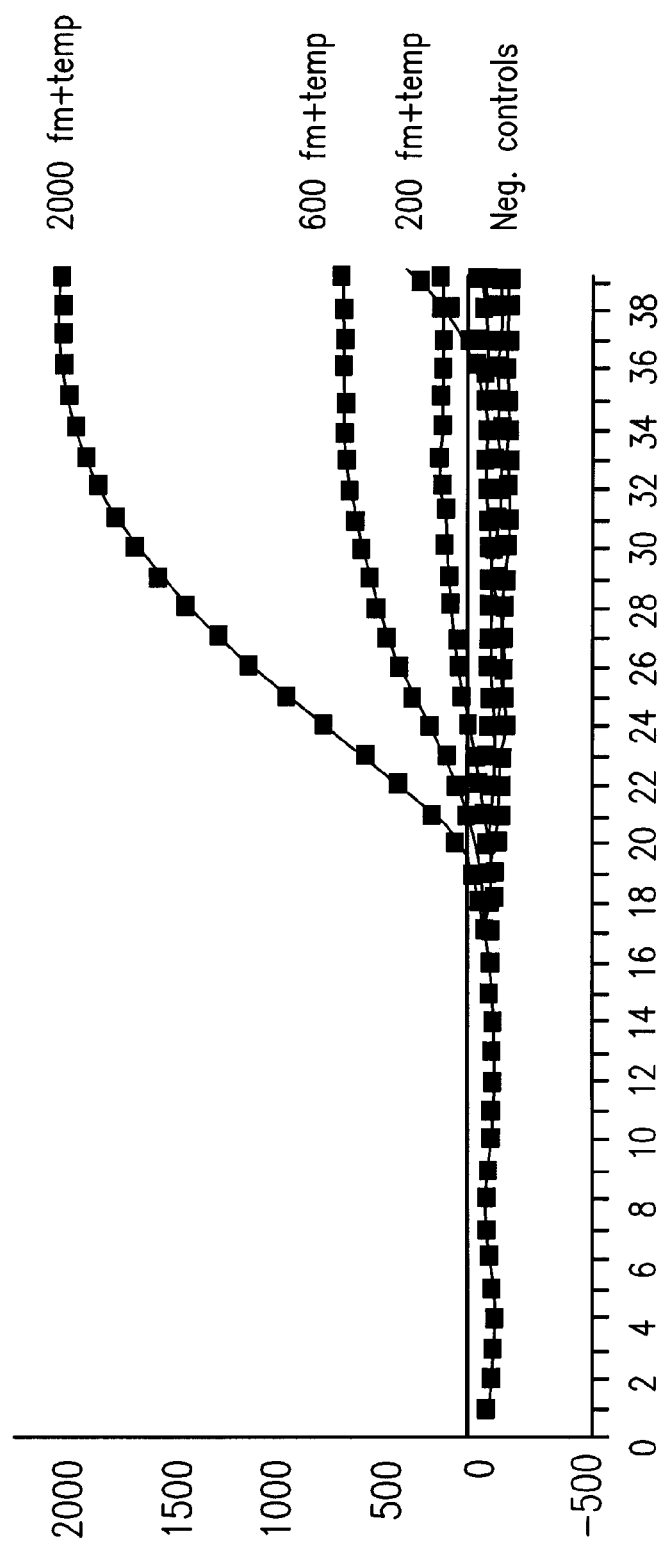

FIG. 1 shows the chemical structure of FAM.
FIG. 2 shows the chemical structure of TAMRA™.
FIG. 3 shows the chemical structure of Cy3™.
FIG. 4 shows flow cytometry results using Cy3™ labeled DNA reporting sequence.
FIG. 5 shows flow cytometry results using a TAM-FAM labeled DNA reporting sequence.

VI. DETAILED DESCRIPTION

Disclosed herein is a simple and rapid method for the multiplexed detection of PCR amplified product by fluorescent microsphere, i.e., bead, flow analysis. Multiplexed detection of PCR amplified products is possible using a fluorescent reporter and a microsphere-based hybridization. A dual detection system is disclosed wherein the presence of target DNA sequences can be identified. A reporting DNA sequence, such as, Taqman®.RTM., real time PCR detection is used in conjunction with microsphere array based multiplexed hybridization identification. First, a real time PCR detection means, such as an Applied Biosystems™ ABI ™ 7700 instrument, is used to detect whether any PCR amplification products were formed during the PCR amplification process. The instrument disclosed in U.S. patent application Ser. No. 10/189319 filed on Jul. 2, 2002, by Colston et al. published as US20030032172, assigned to the same assignee, and hereby incorporated by reference in its entirety, can also be used to detect the presence of PCR amplification products.

A secondary confirmation of the amplification is then accomplished by hybridization of the cleaved DNA reporting sequence fragments resulting from the amplification process and unused reporting sequences to a plurality of fluorescently-labeled microspheres linked to probes complementary to the DNA reporting sequences. The hybrids are then detected using flow cytometry means. Avidin-coated and Carboxylated polystyrene fluorescently-labeled microspheres are effective, such as, Fluorescent microspheres from Luminex Corporation of Austin, Tex. However, fluorescently-labeled microspheres made of other materials and from other manufacturers can also be used. Changes in fluorescence intensity of any hybrid indicates the existence of the target sequence corresponding to the specific probe.

Conventional Taqman® real time PCR reactions take advantage of the 5' to 3' exonuclease activity of the enzyme Taq Polymerase and fluorescence resonance energy transfer (FRET) in order to detect real time PCR amplification of DNA. The Taqman® reaction mixture contains a labeled reporting DNA sequence, e.g., a Taqman® probe, typically 20 to 24 bases long with a fluorophore, i.e., fluorescent reporter dye, on the 5' end and a quencher, i.e., quencher dye, on the 3' end. The reporting DNA sequence, e.g., a Taqman® probe, is complementary to a target DNA sequence. For example in the TAM-FAM labeled reporting sequence, the fluorescent reporter dye, 6-carboxyfluorescein (FAM™), is covalently linked to the 5' end of the oligonucleotide and the quencher dye, 6-carboxy-N,N,N',N'-tetramethylrhodamine (TAMRA™) is linked to the 3' end. FIG. 1 shows the chemical structure of FAM™ and FIG. 2 shows the chemical structure of TAMRA™. During the amplification reaction, the 5' to 3' exonuclease activity of the Taq polymerase cleaves the reporting DNA sequence between the fluorophore and the quencher only if the reporting DNA sequence hybridizes to the target. The reporting DNA sequence fragments are then displaced from the target, and polymerization of the strand continues. The 3' end of the reporting DNA sequence is blocked to prevent extension of the reporting DNA sequence during PCR. The result is that the fluorophore is no longer in close proximity of the quencher and the instrument is able to detect the fluorescent wavelength of the fluorophore. The fluorescence can be measured, and it is in direct proportion to the amount of target DNA being produced. Thus, accumulation of PCR products is detected directly by monitoring the increase in fluorescence of the fluorophore. The increase is determined by comparing the sample signal to a background signal, i.e., a real time PCR reaction without the addition of any target DNA sequence.

The number of fluorophore-quencher pairs available for use during an analysis is limited by their excitation-emission wavelength and whether that wavelength is within the detection parameters of the instrument used. As new dyes are developed, the spectral range of detection continues to expand. The principles involved in the conventional Taqman®.RTM. 5' exonuclease assay are described in more detail by Holland et al in, Detection of specific polymerase chain reaction product by utilizing the 5'-3' exonuclease activity of Thermus aquaticus DNA polymerase, Proc Natl Acad Sci USA 88 (16):7276-80, 1991, which is hereby incorporated by reference in its entirety. A few examples of typical PCR instruments include the ABI prism™7700, the Cepheid Smart Cycler™, and the Bio-Rad iCycler™.

Typically, the PCR reaction mixture comprises 1×PCR buffer, 6 mM of 4.5 M $MgCl_2$, dNTPs (about 2.5 mM each, except about 5 mM for UTP), about 1.25 U of Pt Taq polymerase(GibcoBRL), 400 nM of each primer and 400 nM of each reporting DNA sequence, about 5 µL of sample and PCR water such that the total volume of the mixture is about 25 µL. The enzyme Uracil N-glycosylase (UNG) may be used for decontamination. If UNG is used in the reaction, then about 1U of UNG is used per 50 µL of PCR reaction mixture and an initial cycle of about 50° C. for about 2 minutes is performed. The PCR commences with an initial single cycle of (96° C. for 1 minute). The PCR thermal cycling parameters are dependent on the melting temperatures (Tm's) of the primers, but typically are around 45 cycles of (96° C. for 10 seconds, 60° C. for 60 seconds).

If the instrument disclosed in U.S. patent application Ser. No. 10/189319 filed on Jul. 2, 2002, by Colston et al. published as US20030032172, assigned to the same assignee, then the thermal cycling conditions are one cycle (92.degree. C. for 10 seconds), followed by 40 cycles of (94.degree. C., 5 seconds: 57.degree. C., 15 seconds). The total reaction time is about 10-15 minutes depending on the length of the cycling.

If a dye, such as, FAM™, is used as the fluorophore, then detection of the reporting DNA sequence by flow cytometry will not be possible using a Luminex™ 100 analyzer because FAM™ does not emit at a wavelength seen by the flow cytometer. Two methods are disclosed which overcome this problem. The first method replaces a rhodamine reporter dye, such as, FAM™, at the 5' end with a water-soluble cyanine dye, such as, Cy3™, the structure of which is shown in FIG. 3. It is well known to those in the art that the cyanine dye used in this method fluoresce predominantly at about 570 nin. Both the real time PCR instruments and flow cytometers can detect Cy3™. A Cy3™ quencher such as, Black Hole Quencher-2 (BHQ™-2) from Biosearch Technologies, Inc. replaces the rhodamine quencher dye, such as, TAMRA™, at the 3' end of the reporting DNA sequence. A change in the fluorescence of any reporting DNA sequence indicates the existence of the target DNA sequence specified by the reporting DNA sequence. Multiplex PCR amplification and subsequent hybridization and detection by flow cytometery are possible using a reporting DNA sequence with only a reporter dye, such as, Cy3™, linked to the 5' end and no quencher dye linked to the 3' end. However, if no quencher is linked to the 3' end, then there can be no real time PCR detection coupled to the flow cytometry.

The second method that allows real time PCR detection to be coupled with flow cytometry uses a modified reporting DNA sequence that reverses the location of reporter and quencher dyes. The method positions the reporter dye, e.g., FAM™, on the 3' end and the quencher dye, e.g., TAMRA™, on the 5' end. Other examples of reporter/quencher pairs include Cy3™/BHQ™-2 and Cy5™/BHQ™-3. This method is effective for two reasons: (1) the quencher dye is detectable by flow cytometry and (2) real time PCR detection is not adversely effected by changing the location of the dyes because once the reporting DNA sequence is cleaved, the reporter dye will be detected as long as the quencher dye is no longer in close proximity to it. Detection occurs whether the reporter dye melts off or remains linked to the reporting DNA sequence.

The microsphere-based hybridization reaction can be effectively performed with either Avidin coated or Carboxylated microspheres. Polystyrene microspheres manufactured by Luminex Corporation ordered as Lum-Avidin™ Microspheres are effective, but microspheres made of different materials and/or manufactured by other vendors can also be used. Multiplex analysis is possible because the microspheres are optically encoded with two fluorescent dyes in varying concentrations, thereby creating a population of microspheres, i.e., a set of microspheres, distinguishable by the amount of dyes present within them. Each set of microspheres can be linked to a different oligonucleotide probe that is complementary to a specific target sequence, i.e., the complement of the reporting DNA sequence, used in the PCR reaction. Currently this method allows for the simultaneous detection of up to 100 unique target DNA sequences. This invention, however, has the added benefit of allowing detection of potentially an unlimited number of unique target DNA sequences, for example, greater than one hundred unique target DNA sequences. The number of signatures that are detectable using this invention is limited only by the number of sets of microspheres that are available. As manufacturers become more adept at making microspheres, the number of microsphere sets available for use with this invention will increase and the number of unique target DNA sequences that will simultaneously be detectable will likewise increase. Detection can be accomplished by using a flow cytometer, e.g., a Luminex 100™ analyzer, or other flow cytometry means. Flow cytometry determines whether a reduction in fluorescence occurred which would be indicative of a positive reaction. In contrast, if no reaction occurred, no change in fluorescence will be detected.

As discussed above, the reporter-quencher pair normally used in a Taqman® assay can be modified by locating the quencher at the 5' end of the reporting DNA sequence and locating the fluorophore, also called the reporter, at the 3' end to form a reporting DNA sequence that can be described as a "reverse-Taqman® probe". During this modified-Taqman® amplification reaction, the enzyme will cleave the quencher from the reporting DNA sequence if the target sequence is present. The PCR amplified product containing the reporting DNA sequence fragment linked to the quencher. is added to oligonucleotide probes bound to microspheres, wherein the probes are complementary to the reporting DNA sequences. For example, avidin microspheres ordered from Luminex™ as Lum-Avidin™ Microspheres can be conjugated to Biotin Labeled Probes complementary to the reporting DNA sequences using the protocol obtained from Luminex Corporation. The protocol can be found at the web address luminexcorp.com. An effective microsphere mix contains $10^2$ microspheres per µL in a PCR buffer solution, e.g., 2.5M TMAC, 0-15% SDS, 3 mM EDTA, 75 mM Tris-HCl, pH of 8. Hybridization can be accomplished by combining about 10 µL of the microsphere mix with about 25 µL of the PCR reaction product and mixing at room temperature for about 15 minutes. This method differs from conventional hybridization in that it requires no temperature control since the hybridization products, e.g., the undigested reporting DNA sequences, are already present as single strands in the PCR mix.

EXAMPLES

Example 1

About a 251 µL mixture of about 2.5 µL of 1×PCR buffer, about 6 mM of Sigma® 1 Molar solution of MgCl$_2$ (Sigma® solution number M1787), about 2.5 mM of each dNTPS (Roche™ pharmaceuticals catalog # 1051440 dATP, #1051458 dCTP, #1420470 dUTP, #1051466 d GTP), 1.25 U of Pt Taq polymerase (Life Technologies-Gibco™ BRL catalog # 10955-034), 400 nM of each primer and each reporting DNA sequence labeled with Cy3™ on the 5' end and no quencher on the 3' end (dilution of the reporting DNA sequence is dependant on the signal intensity, the amount typically used is in the range 35 nM to 100 nM determined by a simple titration experiment), about 5 μL of sample and the balance PCR water (Sigma® W4502). An initial single cycle of 96° C. for 1 minute was used followed by 40 cycles of the PCR thermal cycling parameters for Erwinia herbicola (Eh), i.e., 94° C. for 15 seconds: 57° C. for 15 seconds using an ABI™7700.

A microsphere mix was prepared comprising $10^2$ microspheres per μL in a PCR buffer solution, e.g., 2.5M TMAC, 0-15% SDS, 3 mM EDTA, 75 mM Tris-HCl, pH of 8. Hybridization was accomplished by combining about 10 μL of the microsphere mix with about 25 μL of the PCR reaction product and mixing at room temperature for about 15 minutes. The hybridization products were then analyzed using a Luminex 100™ analyzer. Referring to FIG. 4, Erwinia herbicola (Eh) specific sequences were detected by a Cy3™ fluorescent reporter labeled reporting DNA sequence.

Example 2

About a 25 μL mixture of about 2.5 μL of 1×PCR buffer, about 6 mM of Sigma® 1 Molar solution of MgCl$_2$ (Sigma® solution number M1787), about 2.5 mM of each dNTPS (Roche™ pharmaceuticals catalog # 1051440 dATP, #1051458 dCTP, #1420470 dUTP, #1051466 d GTP), 1.25 U of Pt Taq™polymerase (Life Technologies~Gibco™BRL catalog # 10955-034), 400 nM of each primer and 80 nM of each reporting DNA sequence, about 5 μL of sample containing Eh and Bg and the balance PCR water (Sigma® W4502). The reporting DNA sequence concentrations have to be more dilute than in conventional assays to keep the signal in the linear range. If the reporting DNA sequence is too concentrated in the reaction then one will not see a clear positive. An initial single cycle of 96° C. for 1 minute was used followed by 40 cycles of the PCR thermal cycling parameters for Erwinia herbicola (Eh), i.e., 94° C. for 15 seconds: 57° C. for 15 seconds, using an ABI™7700.

A microsphere mix was prepared containing about $10^2$ microspheres per μL in a PCR buffer solution of 2.5M TMAC, 0-15% SDS, 3 mM EDTA, 75 mM Tris-HCl, pH of 8. Hybridization was accomplished by combining about 10 μL of the microsphere mix with about 25 μL of the PCR reaction product and mixing at room temperature for about 15 minutes. The hybridization products were then analyzed using a Luminex 100™ analyzer. FIG. 5 demonstrates how the assay specifically detected only the Eh amplification and not the unrelated *Bacillus globigii* amplification.

While a particular embodiment of the invention has been illustrated and described, along with a listing of potential embodiments therefore and particular parameters, to exemplify and teach the principles of the invention, such are not intended to be limiting. Modifications and changes may become apparent to those skilled in the art, and it is intended that the invention be limited only by the scope of the appended claims.

We claim:
1. A method for multiplexed detection of PCR amplified products comprising:
    providing a DNA sample having unique target DNA sequences of interest for a sample multiplex PCR amplification reaction,
    providing necessary reagents and primers for said sample multiplex PCR amplification reaction, wherein said reagents and primers comprise at least one unique reporting DNA sequence, each of the at least one unique reporting DNA sequence complementary to a region on a corresponding unique target DNA sequence of interest, wherein each unique reporting DNA sequence includes a fluorescence resonant energy transfer marker,
    forming a sample PCR product by conducting said sample multiplex PCR amplification reaction using said DNA sample, and said reagents and primers, wherein the at least one unique reporting DNA sequence is modified upon hybridization with the corresponding unique DNA target sequence, each modified unique reporting DNA sequence detectably distinguishable from a corresponding unmodified unique reporting DNA sequence,
    forming a microsphere mix comprising a plurality of encoded microspheres, each microsphere having a unique physically-detectable code selected from a number of unique physically-detectable codes detectable by flow cytometry, each microsphere bound to a unique biotinylated oligonucleotide, wherein each unique physically-detectable code corresponds to specific oligonucleotide having a DNA sequence able to hybridize a corresponding unmodified unique reporting DNA sequence
    forming a sample hybridization product by adding said sample PCR product to said microsphere mix,
    forming a background PCR product by conducting a background multiplex PCR amplification reaction using at least one control DNA sequence, the control DNA sequence differing from each of the unique target DNA sequences of interest, wherein said background PCR amplification reaction is run under the same conditions and using the same primers and reagents as said sample PCR amplification reaction,
    forming a background hybridization product by adding said background PCR product to said microsphere mix, wherein the presence or absence of false positives is determined; and
    determining the existence of a number of detected target DNA sequences of interest specified by said reporting DNA sequence by comparing the fluorescence of said sample hybridization product with said background hybridization product using flow cytometry, wherein said number of detected target DNA sequences of interest is not higher than said number of unique physically-detectable codes detectable by flow cytometry.

2. The method recited in claim 1, wherein said detected unique target DNA sequences of interest are simultaneously detected.

3. The method of claim 1, wherein said fluorescence resonant energy transfer marker is a cyanine dye that fluoresces predominantly at about 570 nm.

4. A method for multiplexed detection of PCR amplified products, the method comprising:
    providing a DNA sample having unique target DNA sequences of interest for a sample multiplex PCR amplification reaction,
    providing necessary reagents and primers for said sample multiplex PCR amplification reaction, and at least one unique reporting DNA sequence complementary to a region on each target DNA sequence, wherein the at least one unique reporting DNA sequence includes a fluorescent resonant energy transfer marker comprising a fluorophore quencher pair in an operative relationship to one another,
    forming a sample PCR product by conducting said sample multiplex PCR amplification reaction using said DNA sample having unique target DNA sequences of interest, said reagents and primers, and said at least one unique reporting DNA sequence, wherein upon hybridization of the at least one unique reporting DNA sequence with a corresponding unique DNA target sequence, the at least one unique reporting DNA sequence is modified, and wherein the modified unique reporting DNA sequences contain the quencher and the unmodified unique reporting DNA sequences contain the fluorophore, providing necessary reagents and primers and at least one unique reporting DNA sequence for a background multiplex PCR amplification reaction and forming a background PCR product by conducting said background multiplex PCR amplification reaction using at least one control DNA sequence, wherein said background PCR amplification reaction is run under the same conditions and using the same primers, reagents and reporting DNA sequences as said sample PCR amplification reaction, determining with fluorescence detecting means whether a difference in fluorescence exists between said sample PCR product and said background PCR product, said difference being indicative of the multiplex PCR amplification reaction resulting in the formation of (1) at least one PCR amplification product and (2) at least one modified unique reporting DNA sequence containing said quencher, forming a microsphere mix comprising a plurality of unique optically encoded microspheres, each microsphere bound to a unique oligonucleotide, each microsphere encoded with a unique optical code selected from a number of optical codes detectable by flow cytometry, wherein each optical code corresponds to specific oligonucleotide having a DNA sequence able to hybridize with an unmodified unique reporting DNA target sequence, forming a sample hybridization product by adding said sample PCR product to said microsphere mix, forming a background hybridization product by adding said background PCR product to said microsphere mix wherein the presence or absence of a false positive is determined, determining the existence of unique target DNA sequences of interest specified by said reporting DNA sequence by comparing the fluorescence of said sample hybridization product with said background hybridization product using flow cytometry, thus providing a number of detected unique target DNA sequences wherein said number of detected target DNA sequences of interest is not higher than said number of optical codes detectable by flow cytometry.

5. The method of claim 4, wherein the fluorophore of said fluorophore quencher pair is a cyanine dye that fluoresces predominantly at about 570 nm.

6. A method for multiplexed detection of PCR amplified products comprising:

providing a DNA sample having unique target DNA sequences of interest, the DNA sample for a sample multiplex PCR amplification reaction, providing necessary reagents and primers for said sample multiplex PCR amplification reaction and a background multiplex PCR amplification reaction, and at least one reporting DNA sequence complementary to a region on at least one target DNA sequence of interest wherein the reporting DNA sequence includes a fluorescence resonant energy transfer means, comprising a quencher on the 5' end and a fluorophore on the 3' end, forming a sample PCR product by conducting said sample multiplex PCR amplification reaction using said DNA sample, said reagents and primers, and said unique reporting DNA sequence, wherein upon hybridization of the unique reporting DNA sequence with a corresponding unique DNA target sequence, the unique reporting DNA sequence is modified, the modified unique reporting DNA sequence containing the fluorophore and the unmodified unique reporting DNA sequence containing the quencher, forming a background PCR product by conducting said background multiplex PCR amplification reaction, wherein said background PCR amplification reaction is run under the same conditions and using the same primers, reagents and reporting DNA sequences as said sample PCR amplification reaction, determining with fluorescence detecting means whether a difference in fluorescence exists between said sample PCR product and said background PCR product, said difference being indicative of the multiplex PCR amplification reaction resulting in the formation of (1) at least one PCR amplification product and (2) at least one modified unique reporting DNA sequence containing said fluorophore, forming a microsphere mix comprising a plurality of optically-encoded microspheres bound to a plurality of biotinylated oligonucleotides, wherein each optical code is selected from a number of optical codes detectable by flow cytometry and wherein each optical code corresponds to specific oligonucleotide having a DNA sequence able to hybridize with an unmodified unique reporting DNA target sequence, forming a sample hybridization product by adding said sample PCR product to said microsphere mix, forming a background hybridization product by adding said background PCR product to said microsphere mix, wherein the presence or absence of a false positive is determined; and determining the existence of unique target DNA sequences specified by said reporting DNA sequence by comparing the fluorescence of said sample hybridization product with said background hybridization product using flow cytometry, thus providing a number of detected unique target DNA sequences, wherein said number of detected target DNA sequences of interest is not higher than said number of available optical codes detectable by flow cytometry.

7. The method of claim 6, wherein said fluorophore is a cyanine dye that fluoresces predominantly at about 570 nm.

8. A method for multiplexed detection of PCR amplified products, the method comprising:

providing a DNA sample having unique target DNA sequences of interest, providing unique reporting DNA sequences, each of said unique reporting DNA sequences being fluorescently labeled and complementary to a region on each of said unique target DNA sequences of interest, providing multiplex PCR amplification reagents and primers for a multiplex PCR amplification reaction of said DNA sample, contacting said DNA sample with said reagents and primers and with said unique reporting DNA sequences under multiplex PCR amplification conditions to form a sample PCR product, wherein the unique reporting DNA sequence is modified upon hybridization with a corresponding unique DNA target sequence, the modified unique reporting DNA sequence detectably distinguishable from an unmodified unique reporting DNA sequence, providing a microsphere mix comprising a plurality of encoded microspheres, each of the plurality of encoded microsphere encoded with a unique physically-detectable code selected from a number of available unique physically-detectable codes detectable by flow cytometry, each of the plurality of encoded microsphere bound to a unique biotinylated oligonucleotide, each unique biotinylated oligonucleotide able to hybridize the unmodified unique reporting DNA sequences, contacting said sample PCR product with said microsphere mix to form a sample hybridization product, the sample hybridization product comprising microspheres having a sample microspheres hybridization fluorescence, providing a control DNA sequence, the control DNA sequence differing from each of the target DNA sequences of interest, contacting said control DNA sequence with said multiplex PCR amplification reagents and primer and with said plurality of unique reporting DNA sequence, under said multiplex PCR amplification conditions to form a background PCR product contacting said background PCR product with said microsphere mix to form a background hybridization product, the background hybridization product comprising microspheres having a background microsphere hybridization fluorescence, and detecting a number of unique DNA sequences of interest by comparatively detect the sample microspheres hybridization fluorescence with the background microsphere hybridization fluorescence using flow cytometry, the detected number of unique DNA sequences of interest not higher than the number of available unique physically detectable codes detectable by flow cytometry.

9. The method of claim 8, wherein said unique DNA sequences of interest are simultaneously detected.

10. The method of claim 8, wherein said fluorescently labeled unique reporting DNA sequences are labeled with a cyanine dye that fluoresces predominantly at about 570 nm.

* * * * *